United States Patent [19]
Snow et al.

[11] Patent Number: 5,583,206
[45] Date of Patent: *Dec. 10, 1996

[54] CHELATING POLYMERS

[75] Inventors: Robert A. Snow, West Chester; David L. Ladd, Wayne; John L. Toner, Downingtown, all of Pa.

[73] Assignee: Sterling Winthrop, New York, N.Y.

[ * ] Notice: The portion of the term of this patent subsequent to Nov. 30, 2014, has been disclaimed.

[21] Appl. No.: 348,197

[22] Filed: Nov. 28, 1994

Related U.S. Application Data

[63] Continuation of Ser. No. 961,146, Oct. 14, 1992, abandoned.

[51] Int. Cl.$^6$ ..................................................... C07F 5/00
[52] U.S. Cl. ..................................... 534/16; 534/15
[58] Field of Search ................... 424/1.65, 9.322, 424/9.323; 534/10, 15, 16; 436/173, 806; 128/653.4

[56] References Cited

U.S. PATENT DOCUMENTS

| | | | |
|---|---|---|---|
| Re. 30,885 | 3/1982 | Rieder | 252/34 |
| 3,562,161 | 2/1971 | Caserio et al. | 252/51.5 |
| 3,859,337 | 1/1975 | Herz et al. | 260/500.5 |
| 4,407,978 | 10/1983 | Kahovec et al. | 521/56 |
| 4,423,158 | 12/1983 | Porath | 521/32 |
| 4,556,689 | 12/1985 | Murakami et al. | 525/54.1 |
| 4,602,097 | 7/1986 | Curtis | 549/27 |
| 4,615,879 | 10/1986 | Runge et al. | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,746,507 | 5/1988 | Quag | 424/9 |
| 4,804,529 | 2/1989 | Bardy et al. | 424/9 |
| 4,814,098 | 3/1989 | Inada et al. | 252/62.51 |
| 4,822,594 | 4/1989 | Gibby | 424/9 |
| 4,826,673 | 4/1989 | Dean et al. | 424/9 |
| 4,859,451 | 8/1989 | Quay et al. | 424/9 |
| 4,859,777 | 8/1989 | Toner | 546/256 |
| 4,909,257 | 3/1990 | Engelstad et al. | 128/654 |
| 4,916,246 | 4/1990 | Felder et al. | 556/1 |
| 4,920,195 | 4/1990 | Kankare et al. | 534/16 |
| 4,933,441 | 6/1990 | Gibby | 536/112 |
| 4,943,523 | 7/1990 | Stavrianopoulos | 435/7 |
| 4,963,344 | 10/1990 | Gries et al. | 424/9 |
| 4,972,837 | 11/1990 | Engelstad et al. | 562/444 |
| 4,980,148 | 12/1990 | Dean | 424/9 |
| 4,980,502 | 12/1990 | Felder et al. | 424/9 |
| 4,985,233 | 1/1991 | Klaveness et al. | 424/9 |
| 4,986,980 | 1/1991 | Jacobsen | 424/9 |
| 5,057,302 | 10/1991 | Johnson et al. | 424/1.1 |
| 5,077,037 | 12/1991 | Wallace | 424/9 |
| 5,141,966 | 8/1992 | Porath | 521/32 |
| 5,202,423 | 4/1993 | Kankare et al. | 530/391.5 |
| 5,281,704 | 2/1994 | Love et al. | 540/465 |
| 5,285,719 | 1/1995 | Unger | 528/272 |
| 5,324,825 | 6/1994 | Kankare et al. | 534/16 |
| 5,367,080 | 11/1994 | Toner et al. | 546/257 |
| 5,407,657 | 4/1995 | Unger | 424/9 |

FOREIGN PATENT DOCUMENTS

| | | |
|---|---|---|
| 0200467 | 11/1986 | European Pat. Off. . |
| 0450742 | 5/1991 | European Pat. Off. . |
| 0430863 | 6/1991 | European Pat. Off. . |
| 0466200 | 1/1992 | European Pat. Off. . |
| 9004384 | 10/1988 | WIPO . |
| 9001024 | 2/1990 | WIPO . |
| 9115753 | 10/1991 | WIPO . |
| 9118630 | 12/1991 | WIPO . |
| WO93/06148 | 4/1993 | WIPO . |

OTHER PUBLICATIONS

Yokoyama et al, "Molecular Design for Missle Drug . . . " Makromol. Chem. 190, 2041–2054 (1989).

Schuhmann–Giampieri et al, "In Vivo and In Vitro Evaluation of Gd–DTPA–Polylysine . . . " Investigative Radiology, 969–974, (1991).

Marchal et al, "MR Angiography with Gadopentetate . . . " AJR:155, 407–411 (1990).

Mutter, "Soluble Polymers in Organic Synthesis: I. Preparation of Polymer Reagents . . . " Tetrahedron Letters, 31, 2839–42 (1978).

Harris et al, "Synthesis & Characterization of Poly(Ethylene Glycol) Derivatives." J. of Poly. Science, 22, 341–352 (1984).

Shen et al, "Copolymeric MR Contrast Agents", J. Mag. Res. IM., 2, 115 (1992).

Chemical Patents Index, Basic Abstracts Journal, Section Ch, Week 8825, Aug. 17, 1988, Derwent Publications Ltd., London, GB; Class C88, AN 88–173082.

*Primary Examiner*—John Kight, III
*Assistant Examiner*—Lara E. Chapman
*Attorney, Agent, or Firm*—Fish & Richardson PC

[57] ABSTRACT

In accordance with this invention, there is provided a polymer comprising units comprising the residue of a chelating agent linked to a poly(alkylene oxide) moiety, and a method for the preparation thereof. The polymer is particularly useful in therapeutic and diagnostic imaging compositions and as an antistatic agent.

5 Claims, No Drawings

CHELATING POLYMERS

This application is a continuation of U.S. application Ser. No. 07/961,146, filed Oct. 14, 1992 now abandoned.

CROSS REFERENCE TO RELATED APPLICATIONS

Reference is hereby made to commonly assigned U.S. patent application Ser. No. 07/960,746, pending, entitled MR IMAGING COMPOSITIONS AND METHODS and U.S. patent application Ser. No. 07/960,745, now abandoned, entitled THERAPEUTIC AND DIAGNOSTIC IMAGING COMPOSITIONS AND METHODS filed concurrently herewith.

FIELD OF THE INVENTION

This invention relates to novel chelating polymers containing poly(alkylene oxide) moieties and methods for the preparation thereof.

BACKGROUND OF THE INVENTION

Poly(ethylene glycols)(PEGs) and derivatives thereof are finding a rapidly expanding range of chemical, biomedical, and industrial applications resulting from their low cost and useful properties, such as solubility in aqueous and organic solvents, metal complexing ability, biological compatibility and ease of site specific chemical modification. Such polymers have been employed, for example, as matrices for liquid phase peptide synthesis, ligands for water soluble transition metal complexes and drug carriers.

With the development of new application areas, there is a growing demand for new and improved PEG derivatives which can be tailored to meet user requirements.

Inada et al, U.S. Pat. No. 4,814,098 disclose a conjugate comprising a magnetic material and a physiologically active substance bound to each other through a poly(ethylene glycol) derivative.

Mutter, Tetrahedron Letters, 31, 2839–2842 (1978) describes a procedure to convert the terminal hydroxyl groups of PEG to reactive primary amino groups and the preparation of a number of reagents bound to PEG-NH$_2$. However, there is no suggestion of a polymer containing units comprising a poly(alkylene oxide) moiety linked to a chelating group.

Harris et al, J. Polymer. Science, 22, 341–352 (1984) describe various PEG derivatives including PEG-amine. However, there is no suggestion of a polymer containing units comprising a poly(alkylene oxide) moiety linked to a chelating group.

European Patent Application 200,467 describes superoxide dismutase chemically modified with poly(alkylene oxide) which can be used to remove toxic substances derived from oxygen from the blood circulation. The modified superoxide dismutase has a molecular structure in which both ends of a poly(alkylene oxide) molecule are attached to the superoxide dismustase.

SUMMARY OF THE INVENTION

We have discovered that novel chelating polymers which find particular utility in therapeutic and diagnostic imaging compositions can be prepared by contacting reactive poly(alkylene oxides) with chelating agents or precursors thereof containing reactive functionality.

More particularly, in accordance with this invention, there is provided a polymer comprising units comprising the residue of a chelating agent linked to a poly(alkylene oxide) moiety. The polymer preferably comprises units having the structure I:

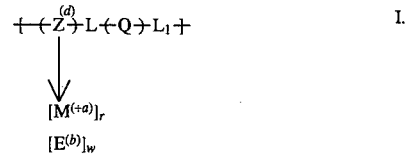

wherein:

Z is the residue of a chelating agent;

Q is a poly(alkylene oxide) moiety;

L and L$_1$ independently represent a chemical bond or a linking group;

$M^{(+a)}$ is one or more cations having a total charge of +a;

$E^{(b)}$ is one or more counterions having a total charge of b;

w is 0 or 1;

r is 0 or 1;

d is the total charge on the linked residue of the chelating agent; and a=d+b.

In another aspect, this invention provides a method of preparing the above-described polymer which comprises contacting a reactive poly(alkylene oxide) species with a chelating agent or precursor thereof containing reactive functionality in a non-reactive solvent and optionally contacting said polymer with a source of metal ions.

It is an advantageous feature of this invention that novel polymers are provided having particular utility in therapeutic and diagnostic imaging compositions.

It is another advantageous feature that a wide variety of polymers of specified composition, size and molecular weight can be prepared in accordance with this invention.

Other advantageous features of this invention will become readily apparent upon reference to the following descriptions of preferred embodiments.

DESCRIPTION OF PREFERRED EMBODIMENTS

The chelating polymer of this invention is useful as a scavenger for metal ions, as an antistatic agent for use in photographic and magnetic recording elements, and as an additive for paints, coatings and adhesives. In addition, certain polymers of this invention particularly useful as contrast agents for use in magnetic resonance (MR) diagnostic imaging compositions and methods and as therapeutic agents as described further in the above-referenced related applications.

The polymer of this invention comprises units containing the residue of a chelating agent linked to a poly(alkylene oxide) moiety in the backbone of the polymer. The polymer can comprise from 2 to 1000 or more, preferably 3 to 1000 of the above-described units. In preferred embodiments, the above-described units are recurring units.

In formula I above, Q represents a linear or branched poly(alkylene oxide) moiety. Exemplary poly(alkylene oxide) moieties include poly(ethylene oxides), poly(propylene oxides) and poly (butylene oxides). Preferred poly(alkylene oxides) include poly (ethylene oxides) (PEO), poly(propylene oxides) (PPO) and random and block copolymers of PEO and PPO. PEO containing polymers are particularly preferred when it is desired for the final polymer to possess solubility in water. It is also contemplated that the poly(alkylene oxide) moiety can comprise glycerol poly(alkylene oxide) triethers, polyglycidols, linear, block and graft copolymers of alkylene oxides with compatible comonomers such as poly(ethyleneimine-co-ethylene oxide), and grafted block copolymers such as poly(methyl vinyl ether-co-ethylene oxide). The poly(alkylene oxide) moieties have an average molecular weight in the range from about 100–200,000, preferably 250–100,000 and more preferably 250–20,000 daltons. Preferred moieties can be derived from poly(alkylene oxide) moieties which are commercially available in the corresponding diol form and/or can be prepared by techniques well known to those skilled in the art. A particularly preferred class of PEO moieties derived from PEGs can be represented by the structure:

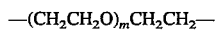

—(CH$_2$CH$_2$O)$_m$CH$_2$CH$_2$— wherein m is 1 to 5,000, preferably 1 to 2500, and more preferably 1 to 500.

The polymer of the invention can comprise the residue of one or more of a wide variety of chelating agents. As is well known, a chelating agent is a compound containing donor atoms that can combine by coordinate bonding with a cation to form a cyclic structure called a chelation complex or chelate. This class of compounds is described in the Kirk-Othmer Encyclopedia of Chemical Technology, Vol. 5, 339–368.

The residues of suitable chelating agents can be derived from and selected to contain chelating elements selected from polyphosphates, such as sodium tripolyphosphate and hexametaphosphoric acid;

aminocarboxylic acids, such as ethylenediaminetetraacetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentacetic acid;

1,3-diketones, such as acetylacetone, trifluoroacetylacetone, and thenoyltrifluoroacetone;

hydroxycarboxylic acids, such as tartaric acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxinesulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids;

Schiff bases, such as disalicylaldehyde 1,2-propylenediimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18] crown-6, (CH$_3$)$_6$-[14]-4,11-diene-N$_4$, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred residues of chelating agents contain polycarboxylic acid or carboxylate groups and include elements present in: ethylenediamine-N,N,N',N'-tetraacetic acid (EDTA); N,N,N',N'',N''-diethylenetriaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylenetriamine pentaacetic acid (CDTPA);

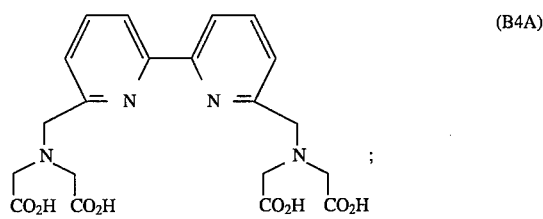
(B4A)

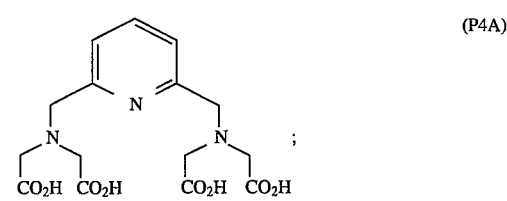
(P4A)

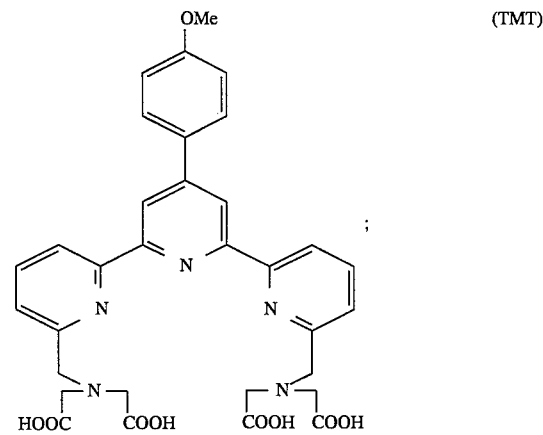
(TMT)

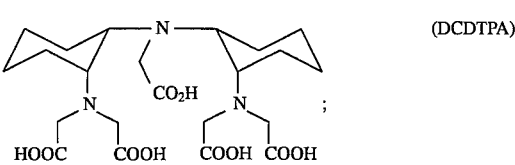
(DCDTPA)

and

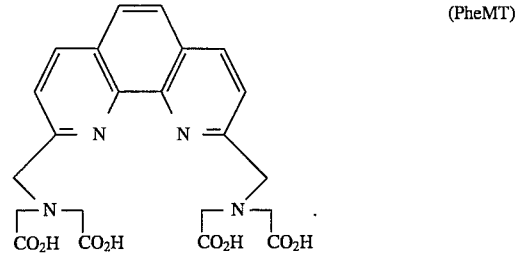
(PheMT)

Other suitable residues of chelating agents are described in PCT/US91/08253, the disclosure of which is hereby incorporated by reference. In formula I above, Z is the residue of one or more chelating agents. If Z is the residue of multiple chelating agents, such agents can be linked together by a linking group such as described below.

The residue of the chelating agent is linked to the poly(alkylene oxide) moiety through a chemical bond or a linking group, i.e., L and $L_1$ in formula I above. Preferred linking groups include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups;
carbonyl;
sulfonyl;
sulfinyl;
ether;
thioether;
ester, i.e., carbonyloxy and oxycarbonyl;
thioester, i.e., carbonylthio, thiocarbonyl, thiocarbonyloxy and oxythiocarbonyl;
amide, i.e., iminocarbonyl and carbonylimino;
thioamide, i.e., iminothiocarbonyl and thiocarbonylimino;
thio;
dithio;
phosphate;
phosphonate;
urelene;
thiourelene;
urethane, i.e., iminocarbonyloxy and oxycarbonylimino;
thiourethane, i.e., iminothiocarbonyloxy, and oxythiocarbonylimino;
an amino acid linkage, i.e., a

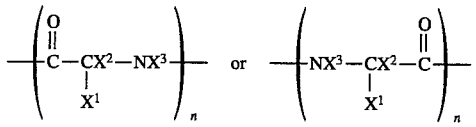

group wherein n=1 and $X^1$, $X^2$ and $X^3$ independently are H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above;
or a peptide linkage, i.e., a

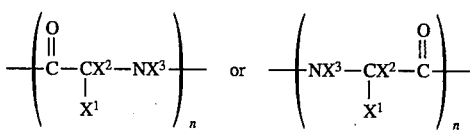

group wherein n>1 and each $X^1$, $X^2$ and $X^3$ are independently represented by a group as described for $X^1$, $X^2$ and $X^3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry. Especially preferred linking groups include unsubstituted or substituted imino groups which when linked to the carbonyl in the residue of a chelating agent forms an amide group.

The linking groups can contain various substituents which do not interfere with the polymerization reaction. The linking groups can also contain substituents which can otherwise interfere with the polymerization reaction, but which during the polymerization reaction, are prevented from so doing with suitable protecting groups commonly known in the art and which substituents are regenerated after the polymerization by suitable deprotection. The linking groups can also contain substituents that are introduced after the polymerization. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; the residue of a chelating group, preferably comprised of elements such as described for Z above but being subtended from the backbone at one covalent site of such elements; or a poly(alkylene oxide) moiety, preferably such as described for Q above but being subtended from the backbone of the polymer at one site of the poly(alkylene oxide) moiety and terminated by substituents selected from, for example, H, OH, alkyl, alkoxy, or elements of a chelating agent as described above.

In a preferred embodiment L and $L_1$ independently represent

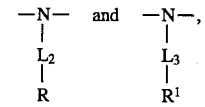

wherein $L_2$ and $L_3$ independently represent a chemical bond or a linking group such as described above, and R and $R^1$ independently represent H; or a substituent attached to the linking group such as described above.

The polymer of the invention can comprise any cation or combination of cations. For example, $M^{(+a)}$ can be $H^+$, in which case the polymer is in its nonmetallized acid form, or a metal ion such as $Li^+$, $Na^+$, $Al^{+3}$, $K^+$, $Ca^{+2}$, $Mg^{+2}$ $Cu^+$, $Cs^+$, $Zn^{+2}$ $Cu^{++}$, $Ag^+$ and $Sn^{++}$, or a basic nitrogen or phosphorus salt, such as a quaternary ammonium or phosphonium salt.

For MR imaging applications, $M^{(+a)}$ preferably represents a paramagnetic metal ion such as an ion of metals of atomic number 21 to 29, 42, 44 and 57 to 71, especially 57 to 71. Ions of the following metals are preferred: Cr, V, Mn, Fe, Co, Ni, Cu, La, Ce, Pr, Nd, Pm, Sm, Eu, Gd, Tb, Dy, Ho, Er, Tm, Yb and Lu. Especially preferred are $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$.

For therapeutic and diagnostic imaging applications, M can be a radioactive metal ion isotope. The radioactive metal ion isotope can be an ion of an isotope of a metal selected, for example, from Sc, Fe, Pb, Ga, Y, Bi, Mn, Cu, Cr, Zn, Ge, Mo, Tc, Ru, In, Sn, Re, Sr, Sm, Lu, Eu, Sb, W, Re, Po, Ta and Tl ions. Preferred isotopes of radioactive metal ions include $^{44}Sc$, $^{64,\ 67}Cu$, $^{111}In$, $^{212}Pb$, $^{68}Ga$, $^{90}Y$, $^{153}Sm$, $^{212}Bi$, $^{99m}Tc$ and $^{188}Re$.

E can be one or more counterions. For example, E can be one or more anions, such as a halide, such as chloride and iodide; sulfate; phosphate; nitrate; and acetate. E can be one or more cations such as $Na^+$, $K^+$, meglumine, and the like. For in vivo applications, nontoxic physiologically tolerable anions are, of course, desirable.

In structure I above, w is 0 or 1, r is 0 or 1, a is an integer preferably from 1 to 4, b is an integer preferably from 0 to 3, and d is an integer preferably from 0 to 4. When E is present, i.e., when w is 1, b most preferably is 1 or 2. d can range up to about 100 when Z comprises the residues of multiple chelating groups. The total positive charge on the cations equals the sum of the total charge on the residue of the chelating group plus the total charge on any counterions E present, i.e., a=d+b.

The metal content in the polymer of the invention can be 0, e.g., when $M^{+a}=H^+$, or it can vary from about 0.9 up to about 30% based on the total weight of the polymer. The metal can be present in an amount of 0.9–30%, preferably 1–25%, and more preferably 2–20% by weight.

The polymer in structure I can be capped at the termini with groups independently selected from Z, Q, L or $L_1$ to which is bound a terminal hydrogen atom, OH, alkyl, alkoxy, or elements of a linking group substituent such as described above. In preferred embodiments, wherein the polymer is a polyamide, the polymer can be capped with groups such as hydrogen or hydroxyl groups or with groups derived from polyamide chain terminating agents such as from monoamines and monoacyl derivatives such as monoanhydrides, e.g., acetic anhydride, or with groups derived from elements of the residue of a chelating group as defined above. It is further contemplated that cyclic polymers, i.e., non-capped polymers can be prepared.

The molecular weight (MW) of the polymer of this invention can vary widely, i.e., from about 1,000 to $10^8$ or greater, as measured by gel permeation chromatography (GPC). The polymer can be prepared in water-soluble, water-dispersible or water-insoluble forms, depending on the intended application. Water-soluble polymers generally are of MW from 1,000 to about 250,000. Water-insoluble crosslinked polymers generally are of MW from $10^5$ to $10^8$.

The polymer of this invention can be prepared by contacting a reactive poly(alkylene oxide) species with a chelating agent or precursor thereof containing reactive functionality in a non-reactive solvent to form the polymer. The poly(alkylene oxide) species can be substituted or unsubstituted.

The preferred reaction conditions, e.g., temperature, pressure, solvent, etc., depend primarily on the particular reactants selected and can be readily determined by one skilled in the art.

Suitable reactive poly(alkylene oxide) species include terminally functionalized poly(alkylene oxide) diamines, poly(alkylene oxide) dihydrazines, poly(alkylene oxide) diisocyantes, poly(alkylene oxide) diols, poly(alkylene oxide) dialdehydes, poly(alkylene oxide) dicarboxylic acids, poly(alkylene oxide) bis(vinyl sulfonyl) ethers, poly(alkylene oxide) diphosphates, poly(alkylene oxide) N,N-dialkylaminophosphoramidates, poly(alkylene oxide) diepoxides, poly(alkylene oxide) dialkoxides, poly(alkylene oxide) disulfonates, poly(alkylene oxide) dihalides and the like. The above-described poly(alkylene oxide) species are linear difunctional species. Tri- and higher multifunctional branched species relating to the above are also useful.

Suitable chelating agents and precursors thereof containing reactive functionality include polycarboxylic acids in dianhydride form, di(sulfonyl chlorides), di(alkyl sulfates), di(vinyl sulfones), diesters and the like. As will be recognized by one skilled in the art, a suitably blocked progenitor to the chelating agent or precursor thereof containing reactive functionality can be contacted with the reactive poly(alkylene oxide) moiety to form the polymer, and then the blocking group can be subsequently removed by techniques known in the art. It is contemplated that additional chelating functional groups can be introduced by suitable chemical modification at the unblocked sites. If hydroxy substituents are to be selectively present in the final polymer, they preferably should be temporarily blocked during polymerization, e.g., by conventional blocking techniques, to minimize formation of undesirable byproducts, e.g., polyesteramide derived therefrom. However, for some purposes, polyesterpolyamides which contain one or more ester linking groups in the backbone of the polymer are contemplated to be useful. The use of condensing agents such as carbodiimides is also contemplated to be useful in the formation of the polymers of this invention.

In a preferred embodiment, the polymer of this invention can be prepared by reacting a linear poly(alkylene oxide) diamine with a precursor of a chelating agent in an internal dianhydride form.

The poly(alkylene oxide) diamine can be prepared by reacting an activated form of the poly(alkylene oxide) with ammonia, a primary amine, a polyamine, an amide, or an azide followed by reduction. The amino group can be introduced by other methods known in the art. Suitable illustrative amines include N-methylamine, amino acids, aminomethyl pyridine, aminomethylthiophene, methoxyethoxyethylamine, methoxyethylamine and aminobenzoic acid. Exemplary useful polyamines include diaminohexane, tris(aminoethyl)amine, and diethylenetriamine.

The linear poly(alkylene oxide) in its diol form is widely available commercially or can be prepared by techniques well known to those skilled in the art. The poly(alkylene oxide) is activated for nucleophilic displacement by reacting it with an activator such as p-toluenesulfonyl chloride, thionyl chloride, thionyl bromide, an alkylsulfonyl chloride, e.g., $CH_3SO_2Cl$, a sulfonic acid anhydride, or any other suitable activator known in the art. The activated form of the poly(alkylene oxide) thus can be a ditosylate, a dichloride, a dibromide, etc.

The activated form of the poly(alkylene oxide) is reacted preferably with a stoichiometric excess of the amine, in an inert solvent preferably at a temperature, e.g., 100°–160° C., and pressure, e.g., 1 to 10 atmospheres, sufficient to drive the reaction to completion. Suitable solvents include dioxane, ethanol, and other alcohols. Thereafter, the poly(alkylene oxide) diamine preferably is isolated, e.g., by evaporation or precipitation, and purified, e.g., by dissolving in a suitable solvent such as methylene chloride, chloroform or trichloroethane, and then washing the solution with an excess of aqueous NaOH, or by any other suitable isolation and purification techniques.

The internal anhydride forms of the chelating agents described above are commercially available and/or can be prepared by techniques known in the art. For example, the internal anhydride forms of EDTA and DTPA are commercially available. The internal anhydride forms of DOTA, DO3A, OTTA, B4A, P4A and TMT can be prepared by techniques known in the art. For example, the anhydrides can be prepared by heating the corresponding acids in acetic anhydride in the presence of pyridine as catalyst. Methods for the preparation of B4A, P4A and TMT are described in U.S. Pat. No. 4,859,777. Mixed anhydrides are also suitable.

The reactive polyalkyleneoxide diamine can be reacted with the internal dianhydride in a non-reactive solvent to form the unmetallized polymer. The reaction conveniently can take place at approximately room temperature and atmospheric pressure. However, higher and lower temperatures and pressures are contemplated. Suitable solvents include dimethylsulfoxide, dimethylformamide, acetonitrile, chloroform, dichloromethane and 1,2-dichloroethane. The nonmetallized polymer preferably is isolated and then purified, e.g., by diafiltration.

The metallized polymer can be formed by contacting the unmetallized polymer sequentially or simultaneously with one or more sources of metal ions. This can be conveniently accomplished by adding one or more metal ion solutions or one or more metal ion solid salts or metal ion oxides, preferably sequentially, to a solution, preferably an aqueous solution, of the polymer. Thereafter, or between sequential addition of metal ions, the chelated polymer preferably is diafiltered in water to remove excess unbound metal.

A general reaction scheme for this method of preparing the polymers of this invention and illustrative examples are set forth below.

Alternatively, the polymer can be prepared in a condensation polymerization reaction between a suitable diamine and a diacid containing the metallized chelating group, in a suitably activated form, e.g., in the form of an activated diester.

The molecular weight of the polymer product depends upon many factors including, for example, the molecular weight of the starting poly(alkylene oxide) moiety, the presence or absence of reactive polymerization chain terminating agents (such as monoanhydrides or monoamines in the case of polyamides) which reduce molecular weight by end-capping the polymer during the polymerization process, the absence or presence of reactive crosslinkers or low molecular weight chain extenders which increase the MW of the polymer during polymerization, and the relative concentrations of the poly(alkylene oxide) and chelator moiety present during the polymerization reaction which in turn affects the number of recurring units in the polymer product. To form the polymer of this invention in a water-insoluble form, the above described procedure can be modified to incorporate a crosslinker, e.g., a crosslinkable tri- or higher polyamine, and/or by adding a reactive crosslinking agent, which can be the reactive chelating moiety, or, e.g., a diacid or higher acid chloride, to the polymerization reaction. The preparation of insoluble and water-soluble polymers of molecular weight 1,000 to $10^8$ can be accomplished by routine experimentation by one skilled in the art of polymer synthesis techniques.

The following examples further illustrate the invention.

Examples 1–12 illustrate the preparation of non-crosslinked polymers of the invention.

EXAMPLE 1

A polymer of the invention (Ia) was prepared in accordance with reaction scheme A as described below.

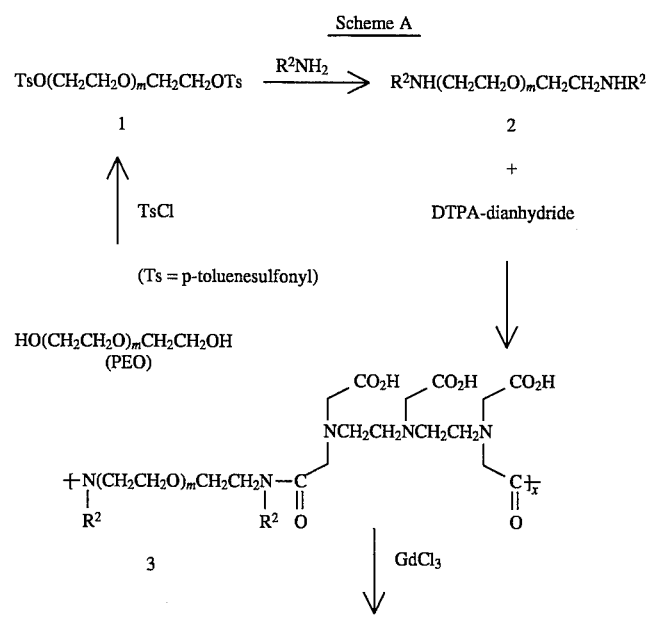

Scheme A

-continued
Scheme A

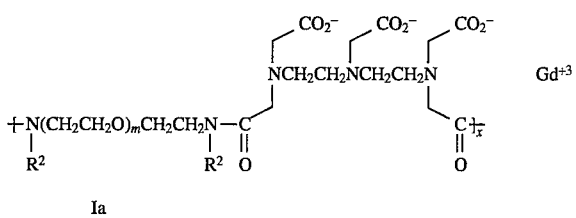

Ia

A solution of 100.0 g (0.0690 mol) of PEO of average molecular weight (MW) 1450 in toluene (1500 ml) was refluxed for 2 hours with azeotropic removal of water. The solution was cooled to 25° C., then treated with triethylamine (46.1 ml, 0.331 mol), 4-dimethylaminopyridine (1.69 g, 0.0138 mol) and p-toluenesulfonyl chloride (57.9 g, 0.303 mol), and then heated for 4 days at 60° C. under an atmosphere of nitrogen. After cooling to room temperature, the reaction mixture was filtered and the filtrate was extracted twice with water. The combined aqueous extracts were washed with ether, then extracted twice with $CHCl_3$. The combined $CHCl_3$ extracts were dried over anhydrous magnesium sulfate and then concentrated to yield 121.3 g of product (1).

A solution of 42.2 g (0.0240 mol) of the ditosylate 1 in 420 ml of dioxane was cooled in an ice bath and a stream of methylamine was introduced over a period of 35 minutes. The reaction mixture was then heated in a sealed stainless steel reactor at 160° C. for 16 hours, cooled to room temperature, and then filtered. The filtrate was concentrated to remove solvent, then treated with water (844 ml) and 1.0N NaOH (95.2 ml) and extracted twice with $CHCl_3$. The combined $CHCl_3$ extracts were dried over anhydrous magnesium sulfate and concentrated to leave 31.0 g of product (2) ($R^2=CH_3$).

A solution of 9.00 g (6.10 mmol) of the bis-(N-methylamine) 2 in 45 ml of dimethylsulfoxide (DMSO) was treated with triethylamine (1.70 ml, 12.2 mmol) and a solution of 2.18 g (6.10 mmol) of diethylenetriaminepentaacetic acid internal dianhydride in DMSO (45 ml). The reaction mixture was stirred at room temperature for 16 hours, then treated with 360 ml of water. The resultant solution was filtered through a 0.45 μm nylon filter and the filtrate was diafiltered against water in a diafiltration cell equipped with a 3000 MW cut-off membrane to leave 170 ml of a solution of (3) ($R^2=CH_3$).

A 160 ml portion of the aqueous solution was treated with a two-fold molar excess of gadolinium(III) chloride hexahydrate, and then was diafiltered against water as described above. Lyophilization of the retentate yielded 8.66 g of product (Ia) ($R^2=CH_3$) of average MW 16,300 daltons (as determined by SEC-HPLC using PEO molecular weight standards). Elemental analysis for $C_{82}H_{156}GdN_5O_{40}\cdot 4H_2O$:

| Element | % Theory | % Found |
|---|---|---|
| C | 47.32 | 47.15 |
| H | 7.94 | 7.89 |
| N | 3.36 | 3.30 |
| Gd | 7.55 | 7.37 |

The relaxivity $(T_1)^{-1}$ of this material at 20 MHz and 40° C. was found to be 6.2 $mM^{-1}s^{-1}$.

Intravenous administration of 100, 200 and 400 mg/Kg to mice resulted in no deaths, no effect on body weight and no abnormalities upon necropsy after 14 days.

The same product, but prepared using radioactive $^{153}Gd$ was employed in biodistribution studies in rats to determine a blood-pool half-life (elimination phase) of 75 minutes.

EXAMPLE 2

In a manner similar to Example 1, a polymeric gadolinium chelate (Ia, $R^2=CH_3$) of average MW 8,010 was prepared from PEO of MW 1000. The blood-pool half-life (elimination phase) was determined to be 48 minutes.

EXAMPLE 3

In a manner similar to Example 1, a polymeric gadolinium chelate (Ia, $R^2=CH_3$) of average MW 16,800 was prepared from PEO of average MW 2000.

EXAMPLE 4

In a manner similar to Example 1, a polymeric gadolinium chelate (Ia, $R^2=CH_3$) of average MW 22,400 was prepared from PEO of average MW 3350. Elemental analysis for $C_{168}H_{328}GdN_5O_{83}\cdot 5H_2O$:

| Elemental | % Theory | % Found |
|---|---|---|
| C | 50.00 | 50.00 |
| H | 8.53 | 8.61 |
| N | 1.75 | 1.71 |
| Gd | 3.94 | 3.78 |

The blood-pool half-life (elimination phase) of this material in rats was determined to be 141 minutes.

EXAMPLE 5

This example describes the preparation of a polymer (Ia) wherein $R^2=H$.

A solution of 15.30 g (11.70 mmol) of ditosylate 1 prepared from PEO of average MW 1000 in 153 ml of absolute ethanol was cooled in an ice bath, and a stream of ammonia was introduced over a period of 30 minutes. The reaction mixture was heated in a stainless steel reactor at 100° C. for 16 hr, cooled to room temperature, and then filtered. The filtrate was concentrated to remove solvent, treated with water (153 ml) and 1.0N NaOH (46.8 ml), and then extracted twice with $CHCl_3$. The $CHCl_3$ extracts were dried over anhydrous magnesium sulfate, filtered, and then concentrated to leave 12.20 g of product (2) ($R^2=H$).

A solution of 11.22 g (11.24 mmol) of the diamine (2) in 56 ml of DMSO was treated with triethylamine (3.13 ml, 22.5 mmol) and a solution of 4.017 g (11.24 mmol) of diethylenetriaminepentaacetic acid dianhydride in DMSO (56 ml). The reaction mixture was stirred at room temperature for 16 hr, and then treated with 448 ml of water. The resulting solution was filtered through a 0.45 μm filter, and the filtrate was diafiltered against water in a diafiltration cell equipped with a 3000 MW cut-off membrane to leave 225 ml of solution.

A 208 ml portion of the aqueous solution was treated with a two-fold excess of gadolinium (III) chloride hexahydrate, and then diafiltered against water. Lyophilization of the retentate yielded 11.58 g of product (Ia, $R^2$=H) of average MW 12,500. Elemental analysis for $C_{60}H_{112}GdN_5O_{30} \cdot 2H_2O$:

| Elemental | % Theory | % Found |
|---|---|---|
| C | 45.70 | 45.95 |
| H | 7.42 | 7.53 |
| N | 4.44 | 3.85 |
| Gd | 9.97 | 10.20 |

EXAMPLE 6

Example 5 was repeated except that the starting PEO had an average MW of 1450. The lyophilized product was determined to have an average MW of 21,900.

EXAMPLE 7

Example 1 was repeated except that B4A-dianhydride was used in place of DTPA-dianhydride. The product (Ib) was determined to have an average MW of 17,600.

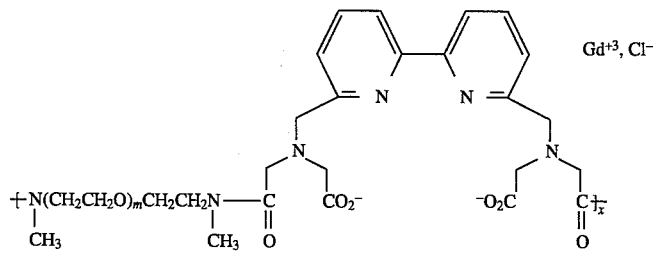

Elemental analysis for $C_{88}H_{156}ClGdN_6O_{38} \cdot 4H_2O$:

| Elemental | % Theory | % Found |
|---|---|---|
| C | 48.69 | 48.56 |
| H | 7.61 | 7.58 |
| N | 3.87 | 3.76 |
| Gd | 7.24 | 7.09 |

EXAMPLE 8

Example 1 was repeated except that P4A-dianhydride was used in place of DTPA-dianhydride. The product (Ic) was determined to have an average MW of 20,000.

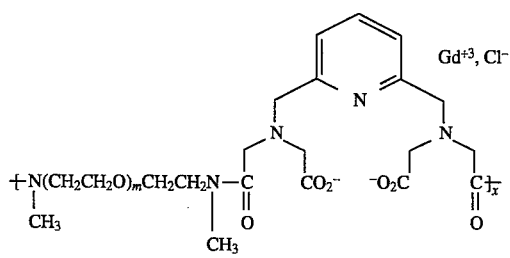

Elemental analysis for $C_{83}H_{153}ClGdN_5O_{38} \cdot 4H_2O$:

| Elemental | % Theory | % Found |
|---|---|---|
| C | 47.61 | 47.38 |
| H | 7.75 | 7.96 |
| N | 3.34 | 3.21 |
| Gd | 7.51 | 7.46 |

EXAMPLE 9

Example 1 was repeated except that $DyCl_3$ was used in place of $GdCl_3$. The lyophilized product was found to have an average MW of 14,800. The relaxivity $(T_2)^{-1}$ of this material at 20 MHZ and 40° C. was found to be 0.109 $mM^{-1}s^{-1}$. Elemental analysis for $C_{82}H_{156}DyN_5O_{40}$:

| Elemental | % Theory | % Found |
|---|---|---|
| C | 48.89 | 48.76 |
| H | 7.80 | 7.87 |
| N | 3.48 | 3.48 |
| Dy | 8.07 | 7.80 |

EXAMPLE 10

Example 9 was repeated except that the starting PEO had an average MW of 2000. The lyophilized product was found to have an average molecular weight of 15,300. Elemental analysis for $C_{106}H_{204}DyN_5O_{52} \cdot 4H_2O$:

| Elemental | % Theory | % Found |
|---|---|---|
| C | 48.46 | 48.71 |
| H | 8.17 | 8.05 |
| N | 2.68 | 2.52 |
| Dy | 6.21 | 6.04 |

EXAMPLE 11

Example 9 was repeated except that the starting PEO had an average MW of 3350. The lyophilized product was found to have an average molecular weight of 20,100. Elemental analysis for $C_{168}H_{328}DyN_5O_{83} \cdot H_2O$:

| Elemental | % Theory | % Found |
|---|---|---|
| C | 51.15 | 50.93 |
| H | 8.48 | 8.45 |
| N | 1.78 | 1.80 |
| Dy | 4.12 | 4.05 |

EXAMPLE 12

Example 5 was repeated except that $DyCl_3$ was used in place of $GdCl_3$. The lyophilized product was found to have an average MW of 45,500. The relaxivity $(T_2)^{-1}$ of this material at 20 MHZ and 40° C. was found to be 0.122 $mM^{-1}s^{-1}$. Elemental analysis for $C_{80}H_{152}DyN_5O_{40} \cdot 4H_2O$:

| Elemental | % Theory | % Found |
| --- | --- | --- |
| C | 46.68 | 46.75 |
| H | 7.83 | 7.69 |
| N | 3.40 | 3.15 |
| Dy | 7.89 | 8.04 |

Examples 13–16 illustrate the preparation of crosslinked polymers of the invention.

EXAMPLE 13

A solution of 15.45 g (8.788 mmol) of ditosylate (1) (prepared from PEO of average MW 1450) in 155 ml of dioxane was treated with 20.4 g (0.176 mol) of 1,6-hexanediamine. The reaction mixture was heated in a stainless steel reactor at 160° C. for 16 hours. The cooled reaction mixture was concentrated to remove solvent, and then treated with water (309 ml) and 1.0N NaOH (35.2 ml). The aqueous solution was washed twice with ether, and then extracted twice with $CHCl_3$. The combined $CHCl_3$ extracts were dried over anhydrous magnesium sulfate, filtered and concentrated at 80° C. at 0.5 mm Hg to remove solvent and excess 1,6-hexanediamine and to leave 12.63 g of product (2) ($R^2 = H_2N (CH_2)_6$).

A solution of 4.00 g (2.43 mmol) of (2) ($R^2 = H_2N(CH_2)_6$) in 44 ml of DMSO was treated with triethylamine (1.35 ml, 9.72 mmol) and a solution of 0.867 g (2.43 mmol) of diethylenetriaminepentaacetic acid dianhydride in DMSO (48 ml). The reaction mixture was stirred at room temperature for 16 hours, and then treated with 384 ml of water. The resulting solution was filtered through a 0.45 μm nylon filter and the filtrate was diafiltered against water in a diafiltration cell equipped with a 10,000 MW cut-off membrane.

The retentate aqueous polymer solution was treated with a two-fold excess of gadolinium(III) chloride hexahydrate and then diafiltered against water as described above. Lyophilization yielded 2.10 g of cross-linked product of average MW 49,800 and containing 8.03% Gd by weight.

EXAMPLE 14

In a manner similar to Example 13, a cross-linked polymeric gadolinium chelate of average MW 36,200 containing 9.30% Gd by weight was prepared from a solution of 3.31 g (2.01 mmol) of (2) ($R^2 = -(CH_2)_6NH_2$) in 76 ml of DMSO, triethylamine (1.12 ml, 8.04 mmol) and a solution of 1.078 g (3.016 mmol) of diethylenetriaminepentaacetic acid dianhydride in DMSO (79 ml).

EXAMPLE 15

In a manner similar to Example 13, a cross-linked polymeric gadolinium chelate of average MW 95,300 containing 11.30% Gd by weight was prepared from a solution of 3.00 g (1.82 mmol) of (2) ($R^2 = -(CH_2)_6NH_2$) in 69 ml of DMSO, triethylamine (1.02 ml, 7.29 mmol) and a solution of 1.303 g (3.645 mmol) of diethylenetriaminepentaacetic acid dianhydride in DMSO (72 ml). The relaxivity $(T_1)^{-1}$ of this material at 20 MHz and 40° C. was found to be 8.55 $mM^{-1}s^{-1}$.

EXAMPLE 16

In a manner similar to Example 13, ditosylate (1) (prepared from PEO of average MW 1450) was reacted with tris(2-aminoethyl)amine to yield (2) ($R^2 = CH_2CH_2N(CH_2CH_2NH_2)_2$).

A cross-linked polymeric gadolinium chelate of average MW 41,400 was prepared from a solution of 0.80 g (0.47 mmol) of (2) ($R^2 = CH_2CH_2N(CH_2CH_2NH_2)_2$) in 8 ml of DMSO, triethylamine (0.39 ml, 2.8 mmol) and a solution of 0.34 g (0.94 mmol) of diethylenetriaminepentaacetic acid dianhydride in DMSO (8 ml). The relaxivity $(T_1)^{-1}$ of this material at 20 MHz and 40° C. was found to be 10.2 $mM^{-1}s^{-1}$.

EXAMPLE 17

In a manner similar to Example 4, a polymeric chelate (3, $R^2 = CH_3$) of average MW 28,900 was prepared from PEO of MW 3350. Polymeric yttrium-90 chelate was prepared by the addition of 1 μCi $^{90}YCl_3$ per μg of polymer followed by a 10-fold excess of non-radioactive $YCl_3 \cdot 6H_2O$. The radiolabeled polymer was purified using a PD-10 (Pharmacia LKB Biotechnology) desalting column. When a PBS solution of the radiolabeled chelate was injected into the tail vein of HT29 tumor bearing nude mice, localization of the chelate into the tumor was evidenced.

The invention has been described in detail with particular reference to certain preferred embodiments thereof, but it will be understood that variations and modifications can be effected within the spirit and scope of the invention.

What is claimed:

1. A polymer comprising polymer repeat units of (1) a poly(ethylene oxide) backbone moiety and (2) a chelant moiety linked to said poly(ethylene oxide) backbone moiety, said polymer repeat units having the structure:

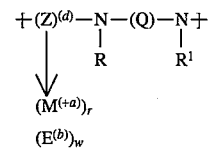

wherein:

Z is said chelant moiety and is a N,N'-[[(2,2'-bipyridine)-6,6'-diyl]bis(methylene)]bis(N-carboxymethyl)glycine or N,N'-[[pyridine-2,6-diyl]bis(methylene)]bis(N-carboxymethyl)glycine;

Q is said poly(ethylene oxide) backbone moiety and has a molecular weight of 250 to 10000:

$M^{(+a)}$ is one or more paramagnetic metal cations having a total charge of +a;

R and $R^1$ independently are H or $CH_3$;

$E^{(b)}$ is one or more counterions having a total charge of b;

w is 0 or 1;

r is 0 or 1;

d is the total charge on the chelant moiety; and a=d+b.

2. The polymer of claim 1, wherein Z is a chelant moiety of N,N'-[[(2,2'-bipyridine)-6,6'-diyl]bis(methylene)]bis(N-carboxymethyl)glycine, r and w are 0, and R and $R^1$ are $CH_3$.

3. The polymer of claim 1, wherein Z is a chelant moiety of N,N'-[[pyridine-2,6-diyl]bis(methylene)]bis(N-carboxymethyl)glycine, r and w are 0, and R and $R^1$ are $CH_3$.

4. The polymer of claim 1, wherein Z is a chelant moiety of N,N'-[[(2,2'-bipyridine)-6,6'-diyl]bis(methylene)]bis(N- carboxymethyl)glycine, $M^{(+a)}$ is $Gd^{+3}$, $Dy^{+3}$, or $Y^{+3}$, $E^b$ is $Cl^-$, r is 1, w is 1, and R and $R^1$ are $CH_3$.

5. The polymer of claim 1, wherein Z is a chelant moiety of N,N'-[[pyridine-2,6-diyl]bis(methylene)]bis(N-carboxymethyl)glycine, $M^{(+a)}$ is $Gd^{+3}$, $Dy^{+3}$, or $Y^{+3}$, $E^b$ is $Cl^-$, r is 1, w is 1, and R and $R^1$ are $CH_3$.

* * * * *